(12) United States Patent
Woldegergis et al.

(10) Patent No.: US 10,271,930 B2
(45) Date of Patent: Apr. 30, 2019

(54) DENTAL BRIDGES AND SUPERSTRUCTURES, AND METHODS FOR MANUFACTURING THEREOF

(71) Applicant: Kulzer GmbH, Hanau (DE)

(72) Inventors: Yohannes Woldegergis, Hanau (DE);
Stefan Hormann, Waechterbach (DE);
Kristofer Frick, Angelholm (SE)

(73) Assignee: Kulzer GmbH, Hanau (DE)

( * ) Notice: Subject to any disclaimer, the term of this patent is extended or adjusted under 35 U.S.C. 154(b) by 354 days.

(21) Appl. No.: 14/361,441

(22) PCT Filed: Dec. 3, 2012

(86) PCT No.: PCT/EP2012/074252
§ 371 (c)(1),
(2) Date: May 29, 2014

(87) PCT Pub. No.: WO2013/079723
PCT Pub. Date: Jun. 6, 2013

(65) Prior Publication Data
US 2014/0342317 A1      Nov. 20, 2014

(30) Foreign Application Priority Data

Dec. 1, 2011  (DE) .................. 10 2011 119 839
Apr. 27, 2012 (EP) ...................... 12165982

(51) Int. Cl.
| A61C 13/10 | (2006.01) |
| A61C 8/00 | (2006.01) |
| A61C 13/00 | (2006.01) |

(52) U.S. Cl.
CPC .......... *A61C 13/102* (2013.01); *A61C 8/0048* (2013.01); *A61C 13/0018* (2013.01); *Y10T 29/49826* (2015.01)

(58) Field of Classification Search
CPC .............. A61C 13/102; A61C 13/0004; A61C 13/0018; A61C 8/0048; Y10T 29/49826
USPC ........................... 433/213, 201.1, 199.1, 223
See application file for complete search history.

(56) References Cited

U.S. PATENT DOCUMENTS

| 1,530,479 | A | * | 3/1925 | Carlson | ..................... F27D 5/00 |
| | | | | | 432/259 |
| 3,861,867 | A | * | 1/1975 | Ouhl | ...................... A61C 13/12 |
| | | | | | 206/562 |
| 3,885,313 | A | * | 5/1975 | Kikuchi | ................. A61C 13/12 |
| | | | | | 269/296 |

(Continued)

FOREIGN PATENT DOCUMENTS

| EP | 2 289 652 | 3/2011 |
| EP | 2 292 357 | 3/2011 |
| WO | WO 2012/064257 | 5/2012 |

OTHER PUBLICATIONS

International Search Report for International Application No. PCT/EP2012/074252 dated Mar. 18, 2013 (2 pages).

(Continued)

*Primary Examiner* — Matthew M Nelson
(74) *Attorney, Agent, or Firm* — Merchant & Gould P.C.

(57) ABSTRACT

The present disclosure provides a dental bridge intermediary structure comprising a superstructure (203) and a reference plate (200), with distance pins (202) connecting the two. A method for producing a dental bridge superstructure (203) is also provided.

7 Claims, 3 Drawing Sheets

(56) References Cited

U.S. PATENT DOCUMENTS

| | | | | |
|---|---|---|---|---|
| 3,958,924 A | * | 5/1976 | Egenolf | F27D 5/0043 |
| | | | | 432/258 |
| 4,136,449 A | * | 1/1979 | Penrod | A61C 19/10 |
| | | | | 432/258 |
| 4,299,567 A | * | 11/1981 | Tanaka | F27D 5/0043 |
| | | | | 432/253 |
| 6,537,066 B1 | * | 3/2003 | Azzaretto | A61C 9/002 |
| | | | | 433/34 |
| 2002/0137003 A1 | * | 9/2002 | Knapp | A61C 1/084 |
| | | | | 433/76 |
| 2009/0081616 A1 | * | 3/2009 | Pfeiffer | A61C 13/0004 |
| | | | | 433/215 |
| 2010/0152873 A1 | | 6/2010 | Dunne et al. | |
| 2010/0291509 A1 | * | 11/2010 | Berggren | A61C 13/0003 |
| | | | | 433/199.1 |
| 2012/0211155 A1 | | 8/2012 | Wehning et al. | |

OTHER PUBLICATIONS

Office Action for European Patent Application No. 12165982.5 dated Aug. 8, 2017.

* cited by examiner

DENTAL BRIDGES AND SUPERSTRUCTURES, AND METHODS FOR MANUFACTURING THEREOF

This application is a National Stage Application of PCT/EP2012/074252, filed 3 Dec. 2012, which claims benefit of Serial No. 10 2011 119 839.7, filed 1 Dec. 2011 in Germany and Serial No. 12165982.5, filed 27 Apr. 2012 in Europe and which applications are incorporated herein by reference. To the extent appropriate, a claim of priority is made to each of the above disclosed applications.

FIELD OF THE INVENTION

This invention pertains in general to the field of an implant arrangement, and in particular to a dental bridge intermediary structure and more particularly to a dental bridge superstructure.

BACKGROUND OF THE INVENTION

In the field of dental implant technology, Cobalt Chrome (CoCr) is a commonly used material. Dental technicians usually cast dental bridge superstructures of CoCr and subsequently burn porcelain surfaces onto them to obtain a dental prosthesis, which may be attached to dental implants in the jaw. However, the casting process is cumbersome as it requires much preparation with moulds, and the precision in the obtained products is relatively low.

An alternate method for producing a superstructure is to mill/cut a raw material, such as a cuboid or cylinder, made of a suitable material, such as CoCr, into the desired shape. However, this technology gives rise to large amount of material spill, and due to the strength of the material, the milling/cutting is very time consuming and the wear on milling/cutting tools is high.

Also, there is a problem in the field regarding the ability to treat superstructures and dental bridges in subsequent treating stations, to improve adaptation between the superstructure or dental bridge and the structure to which it is intended to be attached, since translation between for example different kind of cutters is lacking.

Hence, an improved method for producing dental prostheses would be advantageous and in particular a method allowing for increased flexibility, cost-effectiveness or user friendliness as well as translation between different machineries would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a dental bridge intermediary structure for transfer into a cutter, comprising a reference plate, distance pins, and a dental superstructure, wherein the reference plate comprises a proximal side for arrangement on a sintering piston and a distal working side with a working surface, said distance pins extending distally from the working surface, and said dental superstructure being arranged at distal ends of the distance pins, and a method for producing a dental bridge superstructure, comprising the steps of: forming dental bridge intermediary structure, by sintering distance pins on a distal side of a reference plate and in turn sintering a superstructure on the distal ends of the distance pins; connecting dental bridge intermediary structure to a cutter; and cutting a distal side of the dental bridge intermediary structure with the cutter.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

The following description focuses on an embodiment of the present invention applicable to a dental prosthesis, such as a dental bridge superstructure. However, it is provided that the method may be used for producing all kinds of small scale prostheses.

In the context hereof the term "superstructure" is intended to mean a framework, for attachment directly onto dental implants or on dental abutments, and provides retention for a fixed dental prosthesis or other suitable facing material. Thus, the term encompasses such structures in single or multiple born implant supported artificial tooth crown, bridges, dentures, bridges, etc., as long the above applies.

Figure 1:
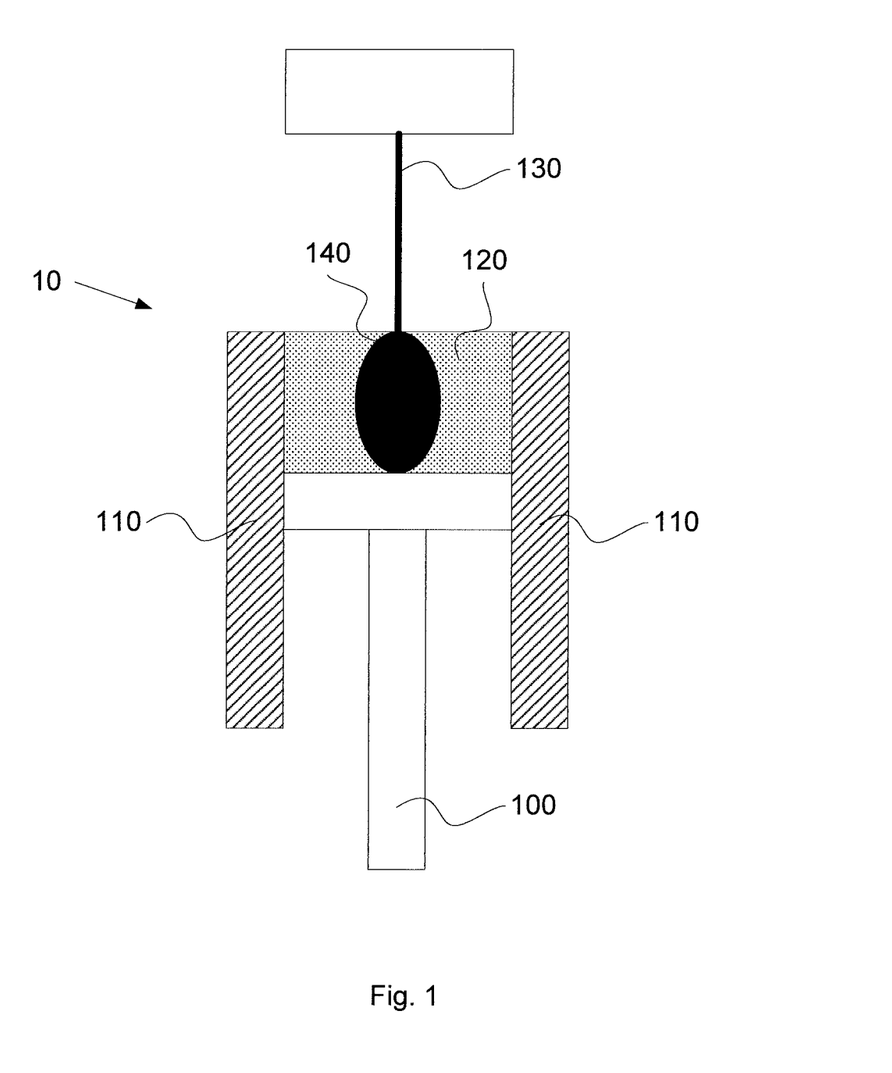
FIG. 1 is an illustration of an instrumental setup for laser sintering according to an embodiment.

Sintering, such as laser sintering, is a method for shaping a three dimensional structure by fusing small particles for example by means of a high power laser. FIG. 1 is a schematic illustration of an instrumental setup for laser sintering. A piston 100 is movably placed in a surrounding structure 110 so that a space is formed with the surrounding structure 110 as walls and the piston 100 as bottom. Small particles of the desired material 120 are added to the space from the top and a movable laser beam 130 is sintering a desired portion of the top layer of the particles into a solid structure. Next, the piston is moved downwards and more material 120 is added on top of the already sintered structure before another run by the movable laser beam 130. By repeating the process, a three dimensional structure 140 is created.

The sintering process is considered not sufficiently precise to use for manufacturing of a dental bridge superstructures. This is due to the fact that the sintering process generates a large amount of heat, which warps the sintered products when they cool. This is considered especially problematic in the field of dental superstructure manufacturing, since the seats for attachment to dental implants are extremely sensitive to lacking preciseness. This, singly or in combination with the fact that the surface of the sintered three dimensional structure 140 is not fine or smooth enough for a dental bridge superstructure, has led the skilled person away from manufacturing dental superstructures by sintering, such as laser sintering.

However, by combining sintering with subsequent cutting or milling, it is possible to conveniently build a three dimensional structure with a smooth surface, without the excess spill from the cutting process, and with improved precision, i.e. high level of detail. It is however difficult to establish and translate the coordinates of the specific parts of the dental bridge superstructure, when moving the product from the sintering step to the cutting or milling step, due to warping of the dental bridge superstructure during sintering. Thus, the boundaries or edges of the sintered superstructure may not exactly correspond to the drawing, which makes it hard to position the superstructure for subsequent cutting, based on these boundaries.

The stereo data with respect to a dental situation of a patient from which the coordinates forming the three dimensional structure come from an inter oral or a 3D scanner. The stereo data is generated in a CAD software. The CAD data obtained may suitbaly be modified by the aid of a library of different geometries of implant connection components, spacer elements, screw channels, screw seats, implant seats etc.

Figure 2:
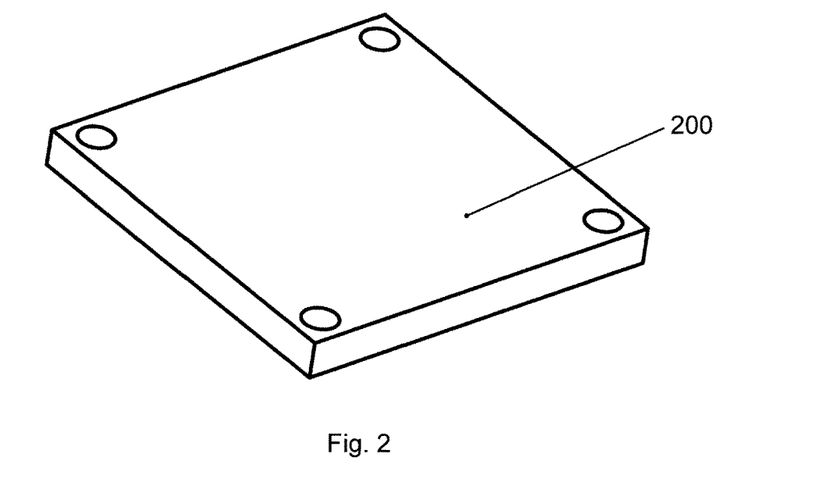
FIG. 2 is an illustration of a reference plate according to an embodiment.

According to one embodiment a reference plate 200, in accordance with FIG. 2, is placed on top of the sintering piston (in accordance with above). The reference plate 200 has a shape and size known to the mill/cutter performing the cutting or milling step. For example, the reference the mill/cutter is provided with the information that the reference plate 200 is rectangular or square, and with what dimensions, i.e. thickness, width and length. This means that when the reference plate 200 is positioned in the mill/cutter, the mill cutter may use the shape and dimension of the reference plate 200 for positioning the reference plate 200, and the structures sintered onto it, in space. The positioning of the reference plate 200 in space in the sintering and milling machine may be obtained by optical measures, by image analysis, or by physical interaction between the borders of the reference plate 200 and a physical recognition means. Thus, the mill/cutter will be able to mill/cut the structures sintered onto the reference plate in accordance with set values, programmed into the mill/cutter. These set values correspond to the values from which the sintering step was performed, such that the mill/cutter may conveniently build a three dimensional structure with a smooth surface, without the excess spill from the cutting process, and with improved precision. The reference plate 200 thus has a proximal side for arrangement onto the sintering piston and a distal working side with a working surface. Preferably, the working surface is substantially planar, for facilitating coordinate transfers from the sintering step into the milling step.

Figure 3:
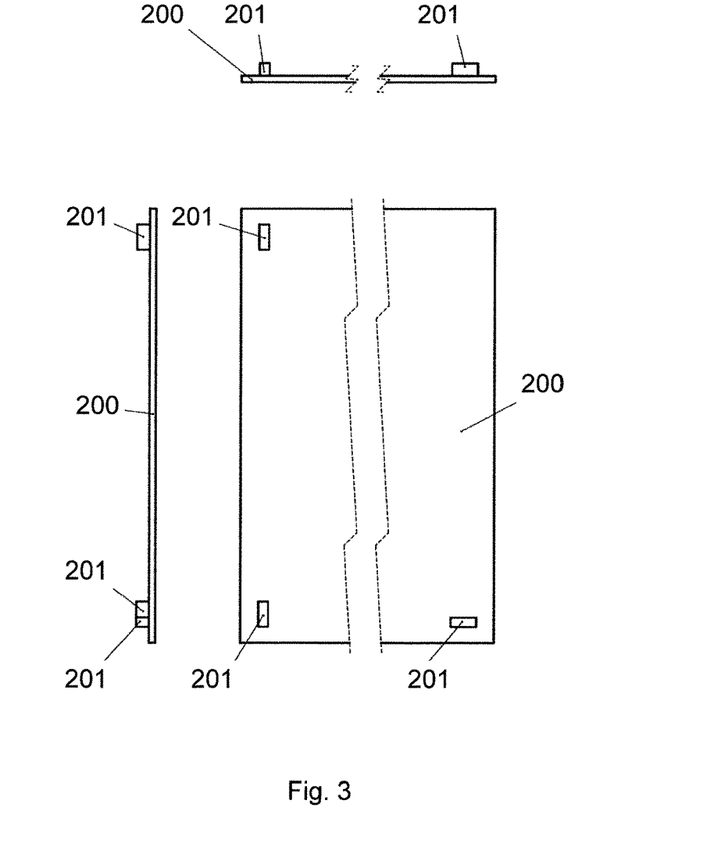
FIG. 3 is another illustration of a reference plate with reference means according to an embodiment.

To further improve the referencing between the milling/cutting step and the sintering step, the reference plate 200 may, in accordance with FIG. 3, be provided with additional reference means 201, such as cavities or protrusions, which also are known in shape and/or shape to the mill/cutter. These cavities and/or protrusions may also aid in connecting the reference plate 200 to the mill/cutter. The reference means 201 may be provided at the distal side of the reference plate during the sintering step. This means that the reference means 201 may be sintered onto the reference plate 200 during the sintering step into the desired shape and dimensions. However, the reference means 201 could also be applied onto the reference plate 200 before sintering, such as through milling or gluing.

These reference means 201 could be recognized in the same way as the reference plate 200 in the sintering and/or the milling machine. The reference means 201 could also be positioned on the proximal side of the reference plate 200. In this case, the reference means 201 are cavities or protrusions that should interact with corresponding protrusions or cavities, respectively, in the sintering and/or the milling machine. The corresponding protrusions or cavities on the sintering and/or the milling machine then are zero-points for the sintering and/or milling machine, such that the sintering and/or milling machine works with these protrusions or cavities as zero-points. The interaction between the cavities or protrusions 201 on the proximal side of the reference plate 200 and the corresponding protrusions or cavities, respectively, on the sintering and/or milling machine could utilize spring pressure to drive wedges against a tapered wedge lock between the two. Air pressure is used to compress the springs and releasing the wedge lock. Clamping is achieved by bleeding the air pressure out of the chuck. To facilitate palletization, the reference means 201, such as a protrusion in form of a clamping knob, is attached to the proximal side of the reference plate 200. In this way, a quick and repeatable clamping between the reference plate 200 and the sintering and/or milling machine could be obtained.

Onto the reference plate 200 the small particles used for sintering is placed, where after the sintering step proceeds.

Suitable materials for manufacturing dental superstructures according to the method described herein are for example selected from the group comprising stainless steels, titanium, aluminum, cobalt-chromium and nickel-based alloys. Preferred materials may be selected from the group comprising cobalt-chromium and titanium. Grain sizes are typically between 10 microns and 150 microns, such as 25 to 60 microns. When sintering with a 300 to 500 W laser, layer thicknesses are suitably in the interval of 20 microns to 100 microns. The processing speed is suitably between 5 and 20 cm$^3$/h. The generated components, the superstructure 203, the distance pins 202, etc. have a homogeneous and monolithic structure and relative densities of nearly 100%, especially between 95% to 99.95%, particularly preferably between 97% and 99.5%, in relation to the density of the starting material in solid form. The components are preferably exposed alternately and in rotation. That is, the layer to be exposed is for example exposed at a 90° offset to the previous layer. This has the advantage that less voltage components and result in a better and more accurate connection between the individual layers.

Figure 4:
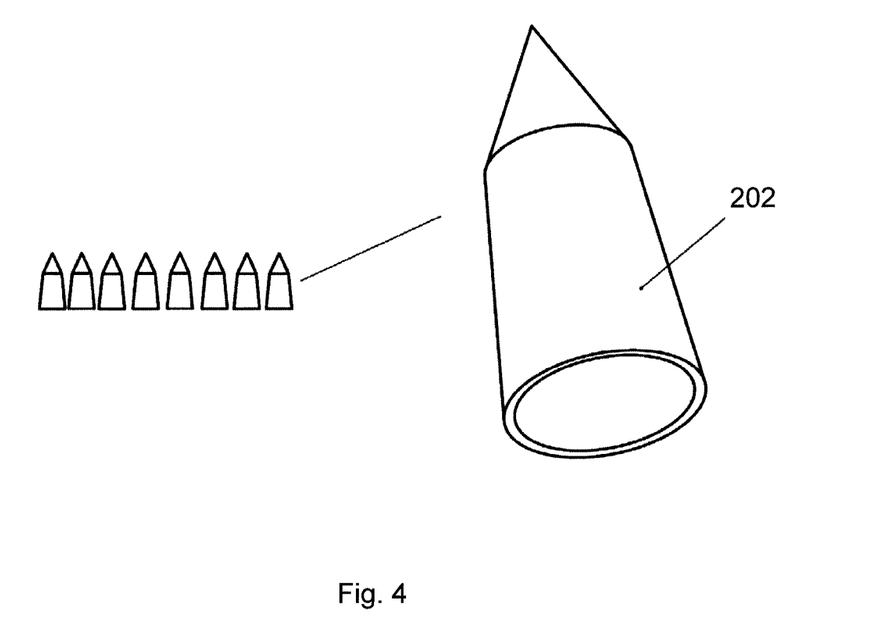
FIG. 4 is an illustration of distance pins according to an embodiment.

Directly on the reference plate 200, distance pins 202, in accordance with FIG. 4, are sintered, optionally together with the reference means 201 if the reference means 201 are to be sintered onto the reference plate 200. The distance pins 202 may be conical, with the cone base connected to the reference plate 200 on the working surface. The distance between the distance pins 202 may preferably be less than 3 mm, such as 1 to 2 mm. At this distance between the distance pins 202, it has been found that warping of the superstructure 203 is effectively prohibited. Additionally, the distance pins 202 may be hollow, to further decrease material consumption during the manufacturing process. To fully support the dental superstructure 203 from warping and to improve heat-exchanging between the sintered structures and their environment, the distal part of the distance pins 202, at the connection zone with the dental superstructure 203, preferably has a width of 0.4 to 1 mm, while the width of the conical base preferably is selected in the interval 1 to 3 mm. Additionally, the distance pins 202 have a proximodistal extension of in the interval 1 to 4 mm, to provide easy access to these to ensure easy removal of the dental superstructure from the reference plate 200 by cutting the distance pins 202, once the milling step has been performed. Of course, other shapes than conical are equally possible, such as cylinder-shaped or pyramid-shaped, even though conical shapes provides preferred heat-exchanging and support characteristics. The distance pins 202 could be sintered onto the reference plate 200 in the same material as the reference plate 200.

It is possible to use more than one powder material during the sintering process. A first powder fraction could be used to create a first part of the sintering, such as the distance pins 202 and/or the main body 204, while a second powder fraction could be used to sinter a second part of the sintering, such as the spacer element 206.

Figure 5:
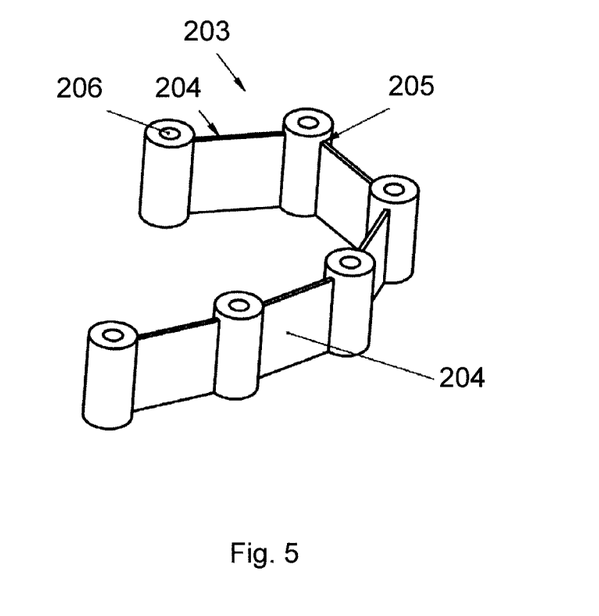
FIG. 5 is an illustration of a dental superstructure according to an embodiment.

The dental superstructure 203, in accordance with FIG. 5, may comprise a main body 204, comprising more than one dental implant seats 205. The implant seats 205 may be positioned on integrated spacer elements 206, which space the main body 204 from the dental implant seats 205, to correspond to the soft tissue on the jaw bone. In this way a monolithic superstructure 203 may be obtained, said superstructure comprising a main body 204, dental implant seats 205, and optionally spacer elements 206, bearing the implant seats 205, respectively.

Onto the distance pins 202 a dental superstructure 203 is in turn sintered. The superstructure 203 could be sintered onto the distance pins 202 in the same material as the distance pins 202 and/or the reference plate 200. The dental superstructure 203 could be sintered to include screw member channels, screw member seats at the bottom of the screw member channels, and/or implant seats 205, to form a monolithic body. Optionally, the dental superstructure 203 is sintered without screw member channels, screw member seats, and implant seats 205. Combinations of these are of course equally possible. Due to the fact that the part of the dental superstructure 203 being the most sensitive to perfect positioning is the implant seats 205, which are at the side of the dental superstructure intended to face the jaw bone, it is preferred to sinter the superstructure 203 onto the distance pins with the intended implant seat positions directed distally. This is so because then the implant seats 205 could be milled with high precision after the sintering step has been performed. It will be very difficult to position the implant seats 205 correctly on the dental superstructure if the positions intended to receive the implant seats 205 are directed proximally, since then the implant seats 205 could first be milled from the dental superstructure 203 once the dental superstructure 203 has been removed from the distance pins 202 and thus the reference plate 200 and/or the reference means 201, whereby reference between the sintering step and the milling step is lost. On the other hand, when the positions intended to receive the implant seats 205 are directed distally after sintering, then the entire reference plate 200 could be moved into the mill/cutter and thus together with appropriate reference means in form of the reference plate 200 and/or the reference means 201.

In one embodiment the superstructure 203 is positioned on the distance pins 202, such that spacer elements 206 and/or implant seats 205, or positions intended to receive implant seats during subsequent cutting/milling, are directed in substantially the same plane as the working surface of the reference plate 200. In this way, the superstructure could be milled on the top side, to form screw channels etc., and on the bottom side, to form implant seats etc., while remaining arranged on the distance pins 202 and/or the reference plate 200.

After the sintering step, the intermediary structure, comprising the reference plate 200, the reference means 201, the distance pins 202, or combinations thereof, together with the superstructure 203, may be posttreated before entering the milling/cutting step. This posttreatment may be performed to release tensions in the material, built up during sintering, etc. The posttreatment may comprise the two steps of heating the intermediary structure to a temperature between 400 to 1000° C., in a protective atmosphere, such as in a suitable inert gas, and discarding oxide layers formed on the sintered product after the heating step by blasting the surface with Al3O2 granules, said granules for example having a mean diameter of 50 to 250 microns.

In this way a structure, such as a dental superstructure intermediary structure, for transfer into the mill/cutter has been obtained. The structure for transfer into the mill/cutter then comprises a reference plate 200 with a proximal side for arrangement on a sintering piston and a distal working side with a working surface. From the working surface distance pins 202 extend distally, and at the distal end of the distance pins 202 the dental superstructure 203 is arranged and connected to the distance pins. The dental superstructure is, according to above, preferably positioned on the distance pins 202 such that the positions on the superstructure 203 intended to receive the implant seats 205 are directed distally. On the working surface reference means 201 are optionally positioned, in accordance with above. The reference plate 200 does not only provide ample reference to transfer coordinates from the sintering step to the milling step, but the reference plate 200, together with the distance pins 202 also prevents warping of the superstructure 203 to some extent, such that it can be assured that the superstructure 203 comprises positions corresponding to the intended implant seats 205. If the superstructure 203 warps to much, there could be a risk that the positions corresponding to the intended implant seats 205 actually were displaced outside the boundaries of the sintered superstructure 203, whereby it would be impossible to obtain a fit between the superstructure 203 and the dental implants.

After the sintering step the structure is transferred to the mill/cutter, and the mill cutter can easily position the sintered superstructure 203 in space thanks to the reference plate 203 and/or the reference means 201. Then, after receiving the intended coordinates of the superstructures and the intended implant seats 205, the mill/cutter mills the implant seats 205 on the superstructure 203. Optionally, the mill/cutter further polishes those surfaces on the superstructure that are reachable. For example other parts of the spacer elements are milled/cut to present the superstructure with a smooth surface for interaction with soft tissue. Milling/cutting is for example performed with appropriate cutting tools in the spindle speed of 10.000 to 40.000 rpm. The processing can be performed with or without cooling. Cooling can be performed with an air stream or a stream of air and additional cooling elements, as known to the skilled person.

After the milling/cutting step, the superstructure 203 may be removed from the reference plate 200 and the distance pins 202. This may be done by simply cutting the distance pins 202 transversally to their proximodistal extension.

In yet another embodiment, the distance pins can be omitted, such that a part of the superstructure during the cutting is cut from the reference plate 200. Thus, it is possible that none or only a part of the superstructure 203, the whole, only a part of or none of the spacer elements 206, and the implant seat 205 is sintered during the sintering step, while the rest of the superstructure 203 is cut from the reference plate 200 during the cutting step.

The sintering may be performed with a device according to FIG. 1, or any other sintering device known to a person skilled in the art. The milling may be performed according to any suitable method, such as CNC cutting.

Thereafter, the side of the superstructure 203 earlier connected to the distance pins 203 may be polished or milled, to obtain an even surface for application of facing material. It is also possible to omit the polishing or milling of this side, if the remainder of the cut distance pins 203 allow for application of the facing material while hiding these remainders. In this situation the remainders of the distance pins 203 may function as anchoring elements for the facing material.

The dental superstructure 203 may be made by Cobalt Chromium (CoCr), through a sintering process, such as laser sintering, in accordance with above.

However, it will be appreciated by a person skilled in the art that the superstructure 203 may also be sintered and subsequently milled from plastics. Such plastic structures would be suitable for use as temporary bridges, after an optional application of a facing material thereon. An advantage with this is that the structure cost less to produce, and the patient would receive a temporary bridge, while the permanent bridge was manufactured. Temporary bridges in plastic material would be advantageous, since exact adjustment with regard to implant positions and angles could be compensated for by the flexibility in the plastic material.

In an embodiment, the superstructure 203 is made from plastic material by sintering or three dimensional printing, which is well known to a person skilled in the art and will thus not be further described.

The reference means 201 comprised in the reference plate 200 may, in accordance with above, be cavities, such as holes, for connecting the reference plate 200 to the cutter. It may also be indentions, corresponding to gripping teeth in a holding device on the cutter or a shape having its correspondence on the cutter, as long as the reference means 201 may guarantee that the position of a certain set of reference coordinates may be transferred from the sintering step to the milling/cutting, such that the milling/cutting unit will know where the cutting/milling action is to be performed to shape and smoothen dental implant connections on the superstructure 203. This is obtained by the reference means 201.

Alternatively, the reference means 201 are merely corresponding to similar negative features on the cutter, such that the reference plate 200 may be positioned correctly on the cutter. An additional alternative is that the reference means 201 is at least one shape that is recognized by a an image processing software, such that the position of the reference plate 200 may translated correctly in the mill/cutter. Then separate attachment means, such as screw holes and corresponding screws or bolts, will preferably be used to fixate the reference plate 200 in the mill/cutter. An advantage with this is that the reference plate 200, with the attached superstructure 203, may be held securely in place by the connection piece. This allows the dental superstructure 203 to be cut by an industrial cutter, such as a computed numerically controlled (CNC) cutter.

In an embodiment, the reference plate 200 is directly fastened in the cutter, thus holding the dental superstructure 203 in position for the cutting process, and the position of the reference plate 200 is established and translated to the mill/cutter via an image processing software. The fastening may be made by means of a conventional chuck, or by any other means as allowed by the machine. Thus, it is possible to establish and translate the coordinates of the specific parts of the dental superstructure 203, when moving the product from the sintering step to the cutting or milling step. Specifically, this is possibly since the reference is no longer dependent on boundaries or edges of the sintered superstructure. Instead, both the drawing and the reference plate 200 and the dental superstructure 203 have specific reference means for this purpose.

In an embodiment, the dental superstructure 203 is automatically positioned in the cutter, based on the location of reference plate 200 and the superstructure 203.

The reference plate 200 and/or the reference means 201 may form a pattern, recognizable by a CNC cutter as the reference or zero position, from which the CNC cutter can navigate around the edges of the dental superstructure 203. The boundaries of the reference plate 200 and/or the reference means 201 are thus code points, occurring both in the drawing of the superstructure 203.

An advantage with this is that it allows for automated cutting, since it is possible for the CNC cutter to orient the dental superstructure 203 in relation to the Computer-aided design (CAD)/Computer-aided manufacturing (CAM) drawings and thus exactly perform the cutting process. This may be achieved by the CNC cutter recognizing the pattern and correlating the pattern to the CAD/CAM drawing, which in turn gives the CNC cutter automatic guiding about where to cut the dental superstructure 203, and more specifically the implant seats 205 on the superstructure 203, by providing a common reference between the drawing and the structure, since the reference plate 200 and the superstructure 203, and optionally the reference means 201, are made in the same piece from the same drawing. Thus, a cut product with a high level of detail may be obtained from a sintered structure, without the need of manual adaptation of the dental superstructures 203 position in the cutter.

Before the sintering, a dental technician supplies an original of the desired bridge superstructure, and a model of the shape of a patient jaw, including the position of the dental implants. The original is scanned according to methods known to a person skilled in the art, to obtain a computer rendering or drawing of its shape. The model is also scanned, to obtain a computer rendering or drawing of the position of the respective implants. Based on these computer renderings or drawings, a CAD/CAM software is used to design a computer rendering or drawing of the dental superstructure 203.

Based on the computer rendering or drawing, a standard laser sintering device is sintering a metal powder, such as powdered CoCr, into a three dimensional dental superstructure 203, connected to the reference plate 200 via the distance pins 202, and optionally with the reference means 201, wherein the reference plate 200 comprises connection means for connecting the reference plate 200 to a cutter, and reference elements, such as the reference plate 200 and/or the reference means 201, for positioning of the superstructure 203 in the cutter. The sintered dental superstructure 203 may be heated after the sintering step to relieve tension that may be the result of the sintering process, which is well known to a person skilled in the art.

During this process, the reference plate 200 and/or the reference means 201 may serve as a support for the superstructure, to prevent or counteract warping of the superstructure 203, while simultaneously providing for coordinate translation between the sintering and the milling/cutting.

Next, the method comprises a step of connecting the reference plate 200 with the superstructure 203 to a machine cutter, such as a CNC cutter. This makes it possible to cut the dental superstructure 203 to obtain a high finish of the structure, and especially of the seats 205 for connection to the dental implants. Also, screw channels may be cut during this process. Screw channels may also be formed through a laser melting process. The connecting may be obtained by a chuck, clamp or other suitable device as known to a skilled person.

The cutting may be guided by reference plate 200 or reference means 201. This is advantageous because the cutter, such as a CNC cutter, may easily find the cutting surfaces, i.e. edges of boundaries on the dental superstructure 203, by correlating these to the position of the reference plate 200 and/or reference means 201 and specifically cut the structure according to the CAD/CAM rendering. Since the whole dental superstructure 203 is part of the CAD/CAM rendering, all the coordinates are easily accessible to the CNC cutter, as known to a person skilled in the art.

The method further comprises a step of cutting the dental superstructure 203 with a cutter, guided by reference plate 200 and/or reference means 201. The cutter may be any cutter, such as a CNC cutter, guided by CAD/CAM software and the reference plate 200 and/or reference means 201.

Since the cutter is guided by the same CAD/CAM rendering as the sintering machine, the cutter will cut the parts of the surface of the dental superstructure 203 resulting from imperfections in the sintering process, which reduces waste. Especially important is to obtain precise implant seats 205 for fastening the superstructure 203 to the dental implants of the patient. To facilitate this, the superstructure 203 is positioned on the distance pins 202 such that the positions for the intended implant seats 205 are directed distally and upwardly from the reference plate 200 and the distance pins 202.

Since the cutter is guided by the reference plate 200 and/or reference means 201, no manual adjustment is needed to position the dental superstructure 203 in the cutter.

In an embodiment, the reference means 201 are protrusions in shape of a "+"-sign, a "−"-sign, or other recognizable shapes, such as square or rectangular. In this way the reference means 201 may also be recognized by an image processing software, to translate the coordinates of the reference means 201, and thus the reference plate 200, and hence also the superstructure 203, to the cutter. Thus, the reference means 201 may mark the zero value for the cutter in relation to the rest of the dental superstructure 203.

The method further comprises a step of separating the superstructure 203 from the reference plate 200, by cutting the distance pins 202, to obtain a dental superstructure 203.

The fastening of the reference plate 200 in the cutter may be obtained by means of a conventional chuck, or by any other means as allowed by the machine.

In an embodiment, the cutting is guided by the same CAD/CAM rendering as the sintering. An advantage with this is that it is easy for the cutter to find the boundaries of the dental superstructure 203 automatically, i.e. without manual measuring or calibration. Thus, the cutting step is faster and results in less waste material.

Since the boundaries, and thus the coordinates, of the reference plate 200 and/or the reference means 201 are present in the CAD/CAM rendering of the dental bridge superstructure 203, which is guiding the cutter, such as a CNC cutter, the cutter will find the boundaries of the dental superstructure 203 automatically, i.e. without manual measuring or calibration.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A dental bridge intermediary structure for transfer onto a cutter, the dental bridge intermediary structure comprising:
   a reference plate comprising a proximal side for arrangement on a sintering piston, and a distal side having a working surface;
   distance pins extending distally from the working surface of the distal side of the reference plate and having distal ends located away from the working surface of the reference plate; and
   a dental superstructure comprising a proximal side and a distal side, the distal side of the dental superstructure is provided with implant seats, and the proximal side of the dental superstructure is sintered onto the distal ends of the distance pins.

2. The dental bridge intermediary structure according to claim 1, wherein the distance pins have a decreasing cross-sectional area in a proximodistal direction.

3. The dental bridge intermediary structure according to claim 2, wherein the distance pins are conical.

4. The dental bridge intermediary structure according to claim 1, wherein said dental bridge intermediary structure is a sintered dental bridge intermediary structure.

5. The dental bridge intermediary structure according to claim 1, wherein said implant seats are milled.

6. The dental bridge intermediary structure according to claim 1, wherein the distal side of the reference plate is provided with reference means.

7. The dental bridge intermediary structure according to claim 6, wherein the reference means is protrusions extending away from the distal side of the reference plate.

* * * * *

UNITED STATES PATENT AND TRADEMARK OFFICE
CERTIFICATE OF CORRECTION

PATENT NO. : 10,271,930 B2  
APPLICATION NO. : 14/361441  
DATED : April 30, 2019  
INVENTOR(S) : Woldegergis et al.

Page 1 of 1

It is certified that error appears in the above-identified patent and that said Letters Patent is hereby corrected as shown below:

On the Title Page (75) Inventors: the second inventor's city is misspelled "Waechterbach" should read --Waechtersbach--

Signed and Sealed this  
Nineteenth Day of November, 2019

Andrei Iancu  
*Director of the United States Patent and Trademark Office*